United States Patent [19]

Braithwaite, deceased et al.

[11] 4,424,388

[45] Jan. 3, 1984

[54] PRODUCTION OF ALCOHOLS BY HYDRATION OF OLEFINS

[75] Inventors: David G. Braithwaite, deceased, late of Tyler, Tex., by Jacqueline M. Braithwaite, executrix; Joe D. Pickle, Flint, Tex.

[73] Assignee: Improtec, Tyler, Tex.

[21] Appl. No.: 392,311

[22] Filed: Jun. 25, 1982

Related U.S. Application Data

[63] Continuation-in-part of Ser. No. 285,306, Jul. 20, 1981, abandoned.

[51] Int. Cl.³ ............................................. C07C 29/04
[52] U.S. Cl. .................................. 568/899; 568/895; 568/898; 568/918
[58] Field of Search ......................................... 568/899

[56] References Cited

U.S. PATENT DOCUMENTS

| | | | |
|---|---|---|---|
| 3,257,469 | 6/1966 | Kovach | 568/899 |
| 3,950,442 | 4/1976 | Vogel et al. | 568/899 |
| 3,994,983 | 11/1976 | Webers et al. | 568/899 |
| 4,012,456 | 3/1977 | Chaplits | 568/899 |
| 4,087,471 | 5/1978 | Bowman et al. | 568/899 |
| 4,096,194 | 6/1978 | Moy et al. | 568/899 |
| 4,182,920 | 1/1980 | Giles et al. | 568/899 |
| 4,234,748 | 11/1980 | Frampton et al. | 568/899 |

FOREIGN PATENT DOCUMENTS 50-137906  11/1975  Japan ................................. 568/899

*Primary Examiner*—J. E. Evans
*Attorney, Agent, or Firm*—Llewellyn A. Proctor

[57] ABSTRACT

A low temperature, low pressure process for the production of alcohol by the hydration of olefins. The olefin is contacted with a sulfonated ion-exchange resin in the presence of water and glycol diethyl solvent to hydrate said olefin, preferably propylene, and form from the olefin the corresponding aliphatic, monohydric alcohol. The solvent, a key and novel feature of the invention, at reaction conditions forms two liquid phases, a glycol diether phase and a water phase. The alcohol forms predominanty in the glycol diether phase and to a lesser extent in the water phase, with the products, inclusive of by product either, being distributed between the two phases. The glycol diethyl phase effectively displaces the equilibrium toward higher alcohol production, and the ether by product suppresses the equilibrium and minimizes formation of the ether product.

6 Claims, No Drawings

PRODUCTION OF ALCOHOLS BY HYDRATION OF OLEFINS

This is a continuation-in-part of application Ser. No. 285,306 filed July 20, 1981 now abandoned.

BACKGROUND OF THE INVENTION

The low molecular weight aliphatic, monohydric alcohols ($C_1$–$C_6$) as a class have many known uses, but today they are being carefully scrutinized for use as fuels. Ethyl alcohol and isopropyl alcohol are of particular importance inasmuch as these alcohols can be burned alone in special engines, or blended with gasoline, or gasoline and benzol, and used in conventional engines as fuel.

Of the numerous methods available for the production of alcohols, one of the more important relates to the hydration of olefins. For example, of the several commercial processes known for the production of isopropyl alcohol, or isopropanol, the most widely used in this country involves reaction between propylene and sulfuric acid. Propylene and sulfuric acid react to form propyl sulfate, the propyl sulfate being hydrolyzed with water to form isopropanol and dilute sulfuric acid. Propylene polymers and di-isopropanol ether are produced as by-products. The isopropanol is separated from the reaction mixture by distillation, and the sulfuric acid is recycled. Considerable energy is required to reconcentrate the sulfuric acid, distill the 91% azeotrope from the products that are formed, and for the ternary azeotropic distillation with di-isopropyl ether to form 99.9% isopropanol. Moreover, the presence of tarry polymers requires that the sulfuric acid be discarded after a production period, or period of operation equal to 25 pounds of 85% sulfuric acid per ton of isopropanol (91%) produced. This process is described in "Industrial Chemicals" by Faith, Keyes and Clark, published by John Wiley & Sons, Inc. in 1965. Ethylene and sulfuric acid can be reacted similarly to produce ethyl alcohol, or ethanol.

Supported phosphoric acid catalysts and sulfonated resins have also been employed for use in the production of alcohols by hydration of olefins. Such processes are described, e.g., in U.S. Pat. No. 2,813,908; U.S. Pat. No. 2,477,380; U.S. Pat. No. 2,891,999; U.S. Pat. No. 2,803,667; U.S. Pat. No. 2,992,189; and U.S. Pat. No. 4,182,920. A commercial process used in Europe by Deutsche Texaco A.G. which employs gel-type sulfonated resins is described in "Hydrocarbon Processing" November 1979 at Page 181. Propylene is directly hydrated to isopropanol in a reactor by downward passage of an admixture of the propylene and water in supercritical state over a bed of ion exchange resin. An intensive exchange between the gas and liquid phases occurs at a temperature between 130°–160° C. and pressure between about 1190-1485 psig, aqueous alcohol and unreacted propylene being drawn off the bottom of the reactor and passed to a high pressure separator wherein the alcohol-containing aqueous phase is separated from a propylene-containing gas phase. The liquid is then passed to a low pressure separator, and the crude alcohol therefrom is distilled; a di-isopropyl by-product being recovered from the top of a first still and isopropyl alcohol recovered as an aqueous azeotropic mixture from a second still. Benzene is used as an entrainer for recovery of the alcohol from the isopropanol-water mixture.

Several problems have limited the commercial acceptane of the sulfonated resin type processing. These include the high pressures and temperature that are required which, in the presence of water and water vapor cause severe disintegration of the resins, with corresponding loss of conversion activity. For example, in the production of isopropanol it is found that a 40% loss of activity occurs over a four hour period when a commercially available "Amberlyst 15" sulfonated macroreticular resin is employed as a catalyst, and the process operated at a temperature of 155°–160° C. and 700 psig propylene pressure.

A need exists for new and improved processes for the production of aliphatic, monohydric alcohols by the hydration of olefins, particularly processes of this type for the production of fuel grade alcohols, especially isopropanol.

It is, accordingly, the primary objective of this invention to satisfy this need.

In particular, it is an object to provide a novel process for the production of fuel grade alcohols, notably ethanol and propanol, by the hydration of olefins of corresponding carbon number in the presence of sulfonated ion-exchange resins.

More specifically, it is an object to provide a novel process for the production of fuel grade alcohols, notably isopropanol, by the hydration of propylene in the presence of sulfonated ion-exchange resins at relatively low temperatures and pressures, to provide better catalyst activity, and selectivity.

These objects and others are attained in accordance with the present invention embodying a process wherein an olefin is contacted with a sulfonated ion-exchange resin in the presence of water and a glycol diether solvent to hydrate said olefin to form the corresponding aliphatic, monohydric alcohol.

Quite unexpectedly, it has been found that the use, as solvents, of certain glycol diethers in the hydration of certain olefins, notably propylene, leads to good conversion and high selectivity. Experimental investigations have shown that these results are largely due to a unique property of these ethers which favorably affects the reaction equilibrium. These solvents thus possess an upper inversion temperature in the region of from about 82° C. to about 93° C. While completely miscible with water at temperatures below about 82° C. to about 93° C. the solvent is immiscible with water above this temperature and forms two liquid phases, a predominantly water phase and a predominantly glycol diether phase. In the production of isopropanol, the preferred alcohol of this invention, the chemical reactions of interest occur in a reaction solvent about 5 percent to about 50 percent water in a glycol diether are as follows:

isopropyl alcohol

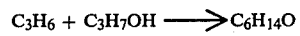

diisopropyl ether

diisopropyl ether

-continued

propylene polymerization products

In the production of isopropanol the solubility of the propylene polymerization products and diisopropyl ether is far greater in the glycol diether phase than in the water phase. Isopropyl alcohol, on the other hand, is highly soluble in both phases. The reaction to form isopropyl alcohol proceeds predominatly in the glycol diether phase and to a much lesser extent in the water phase, primarily because of the low propylene solubility. As the reaction proceeds, the products distribute themselves between both phases. At steady state conditions most of the diisopropyl ether and propylene polymerization products reside in the glycol diether phase. The isopropyl alochol is approximately equally distributed between the phases. Since these are equilibrium reactions, the continuous extraction of the isopropyl alcohol out of the glycol diether phase effectively displaces the equilibrium toward higher conversion of propylene to isopropyl alcohol. Conversely the presence of diisopropyl ether in the reaction phase suppresses the equilibrium and minimizes the ether product. Typically propylene conversion to isopropyl alcohol has been achieved at low pressure with a selectivity of 98 wt. % to 99+ wt. %, whereas in the conventional process with similar catalyst at high pressure, selectivities in the range of only 90–95% are observed.

In all the experimental work with diglycol ethers the absence of propylene polymerization products has been noted even though strenuous efforts have been made to detect them. This result was entirely unexpected and differs completely from the observations made in conventional high pressure reaction systems, using similar catalysts.

Preferable olefins are the low molecular weight hydrocarbons which contain from 2 to about 6 carbon atoms, especially those containing from 2 to about 4 carbons atoms. Exemplary of olefins which can be hydrated to an aliphatic monohydric alcohol containing a similar number of carbon atoms are ethylene, propylene, isopropylene, 1-butene, 2-butene, 3-hexene, 2 ethyl-1-butene, 3 ethyl-2-hexene, and the like; particularly propylene which can be hydrated to form the corresponding aliphatic monohydric alcohol, viz. propanol.

Exemplary of the glycol diethers of this invention the dialkyl ethers of diethylene glycol, such as the dimethyl ether of diethylene glycol, the diethyl ether of diethylene glycol, the dipropyl ether of diethylene glycol, and the like; and the dialkyl ethers of tetraethylene glycol, such as the dimethyl ether of tetraethylene glycol, the diethyl ether of tetraethylene glycol, the dipropyl ether of tetraethylene glycol and the like. The concentration of the organic solvent in the water can be varied over a wide range. Preferably, the solvent is dispersed in the water in concentration ranging from about 5 percent to about 95 percent, more preferably from about 40 percent to about 90 percent, based on the weight of the total of the water and solvent.

Ion-exchange resins suitable in the practice of this invention are strongly acidic, relatively high molecular weight, water-insoluble resins or carbonaceous materials. Preferable resins would contain functional groups such as:

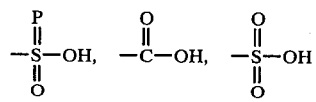

The most desirous resins are the sulfonated polystyrene divinylbenzene or perfluorosulfonated tetrafluorethylene polymer type. Such ion-exchange resins are commercially available, e.g., Amberlite 120 (Rohn and Haas Chemical Company), Chempro C-20 (Chemical Process Company), Dowex 50 (Dow Chemical Company), Nalcite HCR (National Aluminate Corp.), Amberlite IRC-50 (Rohn and Haas Chemical Company), Permutit H-70 (Permutit Company), and the like. In conducting hydration reactions in accordance with this invention, the ion-exchange resin is employed in concentration ranging from about 25 percent to about 500 percent, based on the amount by weight of water and glycol diether solvent added to conduct the reaction.

The reaction is preferably conducted at temperatures ranging from about 110° C. to about 185° C., more preferably at temperatures ranging from about 130° C. to about 150° C., and at pressures ranging from about 100 pounds per square inch (psi) to about 1000 psi, preferably from about 250 psi to about 650 psi, of total pressure. Under these conditions, yields of 99+ percent alcohol can be obtained, with less than 1 percent by-product formation, based on the weight of hydrated olefin. For example, propylene can be hydrated to propanol with 99+ percent yield, with less than 1 percent of the propylene converted to diisopropyl ether and nil polymer formation. This is contrasted with conventional processes for the preparation of propanol from propylene, which do not utilize glycolic diether solvents, providing yields of 91–93 percent propanol, with by-product formation ranging 5–6 percent diisopropyl ether and 2–3 percent polymer.

This invention, its principle and mode of operation, is exemplified and will be better understood by reference to the following examples:

EXAMPLES 1–12

A series of runs (Runs 1–6) were conducted wherein propylene was contacted within a stirred autoclave, in the presence of water and diethylether of tetraethylene glycol, with "Amberlyst 15," a sulfonated ion-exchange resin commercially manufactured and sold by Rohn and Haas Chemical Company. These several runs, summarized in Table I, were each conducted at a temperature of 135° C. and 650–750 pounds per square inch gauge propylene pressure for periods ranging up to 2, or 2½ hours. At these conditions, over these respective periods, high molar concentrations of the propylene was hydrated to isopropanol. The solvent was not only attracted to the sulfonic acid groups of the resin, but also dissolved both the water and the olefin at reaction conditions to produce a more homogeneous system. The homogenous system considerably increases the conversion at lower temperatures and pressures vis-a-vis systems otherwise similar except for the presence of the glycol diether solvent.

TABLE I

| Run No. | Time, Hrs. | Conversion Mole Percent | Quantity Polar Solvent, Grams | Quantity Water Grams | Original Water Analysis Wt. % | Propylene, Grams | Initial Isopropanol, Wt. % | Final Water, Wt. % | Final Weight, Grams | Final Isopropyl Alcohol Wt. % |
|---|---|---|---|---|---|---|---|---|---|---|
| 1 | 2½ | 35 | 525 | 125 | 46.0 | 237 | 0.0 | 21.0 | 758 | 15.6 |
| 2 | 2 | 25 | 400 | 150 | 40.0 | 192 | 3.1 | 22.0 | 587 | 14.8 |
| 3 | 2 | 30.8 | 500 | 200 | 29.8 | 201 | 2.4 | 20.0 | 718 | 14.8 |
| 4 | 2 | 36 | 450 | 230 | 35.9 | 196 | 2.2 | 23.0 | 757 | 15.8 |
| 5 | 2 | 27 | 450 | 175 | 35.8 | 214 | 2.5 | 18.0 | 619 | 14.7 |
| 6 | 2 | 25 | 450 | 175 | 35.9 | 215 | 2.6 | 20.0 | 655 | 13.3 |

In another series of runs (Runs 7-12), the above-identified runs were repeated except that the solvent employed was dimethylether of diethylene glycol. The results obtained did not significantly differ with the use of the lower molecular weight ether.

EXAMPLE 13

In another series of runs (Runs 13A and 13B), "Amberlite 120," a sulfonated ion-exchange resin of greater physical strength, commercially manufactured and sold by Rohn and Haas Chemical Company was employed as the catalytic agent, and propylene again hydrated to propanol.

In a first run with "Amberlite 120," i.e., Run 13A, 100 grams of wet resin was charged into a stirred autoclave, and 200 grams of water then added to the vessel. The reaction was conducted over a period of 2 hours at 800 pounds of propylene pressure and 135°-140° C.

In a second run, Run 13B, a similar quantity of the same catalyst with the same quantity of water was again charged to a stirred autoclave. In this instance, 200 grams of diethylether of tetraethylene glycol was additionally added, and the reaction again conducted at 800 pounds of propylene pressure and 135°-140° C. for a period of 2 hours.

At the end of the two hour period the product from Run 13A was found to contain 0.9 weight percent isopropanol. In sharp contract, at the end of the two hour period in Run 13B the product was found to contain 12.3% isopropanol. Thus, the role of the glycol diether solvent in increasing the selectivity of the sulfonated ion-exchanger resin catalyst is clear.

EXAMPLES 14-15

Another series of runs were made, substantially as described by reference to Example 13, except that in these instances a different ion-exchange resin and a molecular sieve catalyst were substituted for tne Amberlite 120. The results of these runs in terms of isopropanol production are given in Table II.

TABLE II

| Example | Identity of Catalyst | Isopropanol Product, Wt. % |
|---|---|---|
| 14 | Perfluoro sulfonic acid ion-exchange Resin: Manufactured by DuPont; 155° C., 620 psig. | 9.2 |
| 15 | Molecular Sieve Catalyst: Manufactured by Linde, 230° C. 570 psig. | 4.1 |

EXAMPLE 16

The following Table III summarizes the results of five additional runs, Runs 16A-16E, wherein propylene ($C_3H_6$) was hydrated in a continuous reactor to form isopropanol. The reactor contained 400 ml of Amberlite IR-120 acid resin previously conditioned with 30% ether solution of diethyl ether of tetraethylene glycol.

TABLE III

| Run No. | Ether/$H_2O$ (%/%) | Reactor Temp. (Deg C.) | Reactor Pressure (Psig) | % Iso-propanol | % Diisopropyl Ether |
|---|---|---|---|---|---|
| 16A | 85/15 | 135 | 450 | 7.0 | 0.140 |
| B | 85/15 | 150 | 650 | 8.7 | 0.580 |
| C | 85/15 | 120 | 250 | 3.6 | 0.003 |
| D | 60/40 | 135 | 450 | 4.7 | 0.024 |
| E | 10/90 | 138 | 750 | 14.0 | Trace |

EXAMPLES 17-19

In a further series of runs, direct comparisons were made of the selectivity and stability of the glycol diethers of this invention vis-a-vis glycol monoethers. In conducting these runs propylene was contacted at 450 psi in a stirred autoclave in the presence of 100 grams of "Amberlyst 15" and 200 ml of the water and solvent, in equal concentrations. The runs were conducted at 135° F. and 150° F., respectively, with the glycol diether and 135° F. with the glycol monoether. At the end of each run the weight percent conversion to diisopropyl ether (DIPE), the prime product, and the percent conversion to ethanol (ETOH) or methanol (MEOH) were determined, the results of these runs being given in Table IV.

TABLE IV

Selectivity and Stability Comparison
Glycol Diether vs Glycol Monoether

| | | DIPE Wt. % | ETOH Wt. % | MEOH Wt. % |
|---|---|---|---|---|
| Ethylene glycol diethylether | 135° F. | 0.66 | 0.49 | — |
| | 150° F. | 5.25 | 2.67 | — |
| Triethylene glycol diethylether | 135° F. | 0.57 | 1.70 | — |
| Triethylene glycol dimethylether | 135° F. | 1.39 | — | 0.97 |
| | 150° F. | 5.69 | — | 3.67 |
| Diethylene glycol monoethyl ether | 135° F. | 4.68 | 3.01 | — |

These data clearly show the profound advantages of the solvent glycol diethers of this invention vis-a-vis ethers such as used in prior art processes.

It is apparent that certain variations can be made without departing the spirit and scope of the invention. In its essence, the present invention is based on the discovery that a glycol diether solvent can be employed which will permit olefin hydration reactions, especially propylene hydrations to proceed in the presence of an ion-exchange resin at lower temperatures and pressures, while protecting the ion-exchange resin from disintegration. Higher selectivity of the ion-exchange resin catalyst, due to the presence of the solvent, provides high yields of alcohol, with relatively low by-product formation at lower temperature and pressure than can be attributed to processes otherwise similar except that they do not employ such solvents.

Having described the invention, what is claimed is:

1. In a process for the production of alcohol within a reaction medium by hydration of propylene, the propylene being contacted with a sulfonated ion-exchange resin in the presence of water to hydrate and convert said propylene to isopropanol, with by-products inclusive of diisopropyl ether and propylene polymerization products the improvement comprising adding a glycol diether solvent selected from the group consisting of dialkyl ethers of diethylene glycol and dialkyl ethers of tetraethylene glycol to the reaction medium in concentration ranging from about 40 percent to about 90 percent, based on the weight of water and glycol diether solvent and hydrating said propylene at temperatures ranging from about 110° C. to about 185° C. at total pressures ranging from about 100 psi to about 1000 psi sufficient to disperse the water and propylene to form a homogeneous mixture which lies in contact with the ion-exchange resin, the homogeneous mixture containing two dispersed liquid phases, a glycol diether phase and a water phase, the reaction which forms the isopropanol proceeding predominantly in the glycol diethyl phase and to a lesser extent in the water phase, the products being distributed between the two phases, the isopropanol being approximately equally distributed between the phases, the diisopropyl ether and propylene polymerization products being distributed predominantly within the glycol diether phase, whereby continuous extraction of the isopropanol out of the glycol diether phase effectively displaces the equilibrium toward higher isopropanol production, and conversely the presence of diisopropyl ether in the glycol diether phase suppresses the equilibrium and minimizes formation of the diisopropyl ether and other by-product formation.

2. The process of claim 1 wherein the propylene is hydrated at temperatures ranging from about 130° C. to about 150° C., at total pressures ranging from about 250 psi to about 650 psi.

3. The process of claim 1 wherein the reaction is conducted at a temperature ranging from about 130° C. to about 150° C., the total pressure ranges from about 250 psi to about 650 psi, and the yield of isopropanol ranges above about 99 percent.

4. The process of claim 1 wherein the ion-exchange resin employed as a catalyst within the reaction medium is a sulfonated polystyrene divinylbenzene or a perfluorosulfonated tetrafluoroethylene polymer.

5. The process of claim 4 wherein the ion-exchange resin is employed in the reaction medium in concentration ranging from about 25 percent to about 500 percent, based on the amount of water and glycol diether solvent.

6. The process of claim 4 wherein the reaction mixture is maintained at temperatures ranging from about 130° C. to about 150° C., and at pressures ranging from about 250 psi to about 650 psi total pressure in carrying out the hydration reaction.

* * * * *